US010758149B2

(12) United States Patent
Mihajlovic (10) Patent No.: US 10,758,149 B2
(45) Date of Patent: Sep. 1, 2020

(54) NEUROFEEDBACK SYSTEM (71) Applicant: KONINKLIJKE PHILIPS N.V., Eindhoven (NL)

(72) Inventor: Vojkan Mihajlovic, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 606 days.

(21) Appl. No.: 14/421,041

(22) PCT Filed: Aug. 12, 2013

(86) PCT No.: PCT/IB2013/056582
§ 371 (c)(1),
(2) Date: Feb. 11, 2015

(87) PCT Pub. No.: WO2014/027298
PCT Pub. Date: Feb. 20, 2014

(65) Prior Publication Data
US 2015/0216437 A1 Aug. 6, 2015

Related U.S. Application Data (60) Provisional application No. 61/683,270, filed on Aug. 15, 2012.

(51) Int. Cl.
A61B 5/0482 (2006.01)
A61B 5/00 (2006.01)
A61B 5/04 (2006.01)

(52) U.S. Cl.
CPC ........ *A61B 5/0482* (2013.01); *A61B 5/04012* (2013.01); *A61B 5/7221* (2013.01)

(58) Field of Classification Search
CPC combination set(s) only.
See application file for complete search history.

(56) References Cited

U.S. PATENT DOCUMENTS 3,725,690 A 4/1973 Hjorth
3,826,243 A 7/1974 Anderson
(Continued)

FOREIGN PATENT DOCUMENTS

WO 2011017778 A1 2/2011
WO 2011055291 A1 5/2011

OTHER PUBLICATIONS

Fonseca et al: "A Novel Dry Active Electrode for EEG Recording"; IEEE Transactions on Biomedical Engineering, vol. 54, No. 1, Jan. 2007, pp. 162-165.
(Continued)

*Primary Examiner* — Christian Jang
*Assistant Examiner* — Mitchell E Alter (57) ABSTRACT The present invention relates to a neurofeedback system that comprises an electrode (2, 2', 2") for contacting skin (6) of a user (7) for measuring a biofeedback signal (9) of the user (7), a first signal processing unit (3) for determining a signal characteristic (11) of the measured biofeedback signal (9), wherein the signal characteristic (11) represents a neurofeedback, a second signal processing unit (4) for determining a biofeedback signal quality (12) of the measured biofeedback signal (9) by extracting a signal feature of the measured biofeedback signal (9) and calculating a probability of a measurement error for said signal feature, which probability represents the biofeedback signal quality (12), and a feedback unit (5) for providing feedback to the user, wherein the feedback comprises the neurofeedback and a feedback about the biofeedback signal quality (12). A further aspect of the invention relates to a method for supporting a behavior change of a person and a computer program for carrying out said method.

20 Claims, 10 Drawing Sheets

(56) References Cited

U.S. PATENT DOCUMENTS

| | | | |
|---|---|---|---|
| 5,678,560 | A | 10/1997 | Sakamoto et al. |
| 7,433,732 | B1* | 10/2008 | Carney ............... A61B 5/0476 600/544 |
| 2004/0243258 | A1* | 12/2004 | Shattil ................ H04L 27/2628 700/73 |
| 2007/0010729 | A1* | 1/2007 | Virtanen ............ A61B 5/04025 600/391 |
| 2007/0082674 | A1* | 4/2007 | Pedersen .............. H04B 7/026 455/450 |
| 2007/0213599 | A1 | 9/2007 | Siejko et al. |
| 2009/0062680 | A1* | 3/2009 | Sandford ........... A61B 5/04012 600/544 |
| 2010/0249549 | A1 | 9/2010 | Baker et al. |
| 2011/0015496 | A1* | 1/2011 | Sherman ............. A61B 5/0006 600/301 |
| 2011/0295142 | A1* | 12/2011 | Chakravarthy ...... A61B 5/0476 600/544 |

OTHER PUBLICATIONS

Khanna et al: "Miniature Pressure Sensor and Micromachined Actuator Structure Based on Low-Temperature-Cofired Ceramics and Piezoelectric Material"; Materials Chemistry and Physics 87 (2004), pp. 173-178.

Popescu et al: Single Trial Classification of Motor Imagination Using 6 Dry EEG Electrodes; PLoS one, Issue 7, e637, 2007, pp. 1-5.

Sellers et al: "A Novel Dry for Brain-Computer Interface"; Proceedings of the 13th International Conference on Human-Computer Interaction. Part II:Novel Interaction Methods and Techniques, 2009, 10 Page Document.

Luo et al: "A User-Friendly SSVEP-Based Brain-Computer Interface Using a Time-Domain Classifier"; J. Neural Eng. 7 (2010), pp. 1-10.

Van Boxtel et al: "A Novel Self-Guided Approach to Alpha Activity Training"; International Journal of Psychophysiology, 83, (2012), pp. 282-294.

Gautschi: "Piezoelectric Sensorics"; Springer Publishing, 2002.

* cited by examiner

NEUROFEEDBACK SYSTEM

CROSS-REFERENCE TO PRIOR APPLICATIONS

This application is the U.S. National Phase application under 35 U.S.C. § 371 of International Application No. PCT/IB2013/056582, filed on Aug. 12, 2013, which claims the benefit of U.S. Provisional Patent Application No. 61/683,270, filed on Aug. 15, 2012. These applications are hereby incorporated by reference herein.

FIELD OF THE INVENTION

The present invention relates to a neurofeedback system and method to provide neuro feedback to a user. The present invention relates particularly to the field of measuring electrical brain activity, also known as electroencephalography (EEG).

BACKGROUND OF THE INVENTION

Electrical brain activity or EEG is measured by means of EEG electrodes contacting the skin of a user, in particular the scalp of the user. One type of known electrodes are wet or gel electrodes. Another type of known electrodes are dry electrodes (not using gel). The main challenge when applying EEG wet or gel electrodes is to get a good, thus low, contact impedance to the skin. In clinical measurements this is normally done with a (shower-cap like) rubber cap with integrated metal electrodes (e.g. Ag/AgCl coated). The skin underneath these electrodes usually needs to be prepared by degreasing and often additional abrasion (e.g. removal of the dry top layer of the skin, the stratum corneum). The conductive gel is then applied between each electrode and the scalp, typically through a hole in the electrode or cap. This assures a low ohmic contact to the deeper skin layer, the epidermis, and "conversion" from ion current in the body to electron current in the measuring system. Using conductive gel also solves (partly) the problem of the varying distance between the electrode and the skin due to the variation from person to person with respect to the hair layer thickness and the amount of hair, as well as temporal changes of the distance that might occur due to head and/or body motion.

For a lifestyle consumer product as well as for disabled patients and remote monitoring purposes in clinical applications, it is not practical to use this kind of "wet" electrodes. There are attempts to realize dry electrodes that use pin-structured electrodes or similar ways to penetrate the hair and make a galvanic contact to the skin. A problem arises when this type of electrodes has to cope with thick and long hair. In practice, the solutions often result in poor contact to the skin at the scalp and insufficient signal quality. Further, the electrode-skin contact impedance might differ for different electrodes and the variation of the skin contact impedance over time can differ for each electrode, posing a serious threat for practical applications.

An important application for convenient EEG measurements is brain wave sensing technology, such as alpha neurofeedback. Neurofeedback (NF), in particular alpha neurofeedback, is a novel method which may find application areas both in consumer and professional healthcare products. Boxtel et al. "A novel self-guided approach to alpha activity training", International Journal of Psychophysiology, 2011, discloses that neurofeedback induces a feeling of ease in a person without the person feeling the burden of responsibility for his own mental state. This is particularly relevant for a hospital setting, where the user or patient is put at ease in a very subtle way without requiring them to be aware of the effect of neurofeedback. This is important for a hospital setting as it means the patient is not burdened with the feeling of having to relax.

To measure alpha brain wave activity in a convenient way, dry electrodes are necessary. In standard EEG measurements with gel-electrodes, measurements are typically done in controlled conditions, where the experimenter or trained person applies the gel and positions the EEG system on a user's head, checks whether the skin-electrode contact impedance is in range (i.e. less than 10 kΩ), and if the signal looks as expected. In real-life situations where an expert is not available and where the user applies the (headset with) dry electrodes extensive pre-measurements of the signal quality before the actual measurement are not an option. Users are not in the position to perform a thorough check of the signal quality. However, a sufficient signal quality is crucial to prevent users adhering to the wrong neurofeedback.

As a solution to this problem, WO 2011/055291 A1 discloses a device for positioning dry, pin-structured electrodes on a user's scalp. The device features an elastic element to exert pressure on a plurality of electrodes towards the scalp, thereby improving the contact of the electrodes to the skin. One way to further improve the signal quality is to monitor and adjust the electrode-skin contact pressure, which in turn changes the electrode-skin contact impedance.

SUMMARY OF THE INVENTION

It is an object of the present invention to provide a neurofeedback system and method that prevent users from adhering to the wrong neurofeedback. Furthermore, the system and method should be real-time capable.

In a first aspect of the present invention, a neurofeedback system is presented that comprises an electrode for contacting skin of a user for measuring a biofeedback signal of the user, a first signal processing unit for determining a signal characteristic of the measured biofeedback signal, wherein the signal characteristic represents a neurofeedback, a second signal processing unit for determining a biofeedback signal quality of the measured biofeedback signal by extracting a signal feature of the measured biofeedback signal and calculating a probability of a measurement error for said signal feature, which probability represents the biofeedback signal quality, and a feedback unit for providing feedback to the user, wherein the feedback comprises the neuro feedback and feedback about the biofeedback signal quality.

A further aspect of the present invention relates to a signal processor for determining a signal characteristic of the measured biofeedback signal, wherein the signal characteristic represents a neurofeedback, and for determining a biofeedback signal quality of the measured biofeedback signal by extracting a signal feature of the measured biofeedback signal and calculating a probability of the measurement error for said signal feature, which probability represents the biofeedback signal quality.

In a further aspect of the present invention, a method for providing a user with neurofeedback is presented that comprises the steps of measuring a biofeedback signal of the user, determining a signal characteristic of the measured biofeedback signal, wherein the signal characteristic represents a neurofeedback, determining a biofeedback signal quality of the measured biofeedback signal by extracting a signal feature of the measured biofeedback signal and calculating a probability of a measurement error for said signal feature, which probability represents the biofeedback signal quality, and providing feedback to the user, wherein the feedback comprises the neurofeedback and feedback about the biofeedback signal quality.

In yet another aspect of the present invention, there is provided a computer program which comprises program code means for causing a computer to carry out the steps of the method for providing a user with neurofeedback according to the present invention when said computer program is carried out on the computer.

Preferred embodiments of the invention are defined in the dependent claims. It shall be understood that the claimed signal processor, method and computer program have similar and/or identical preferred embodiments as the claimed device and as defined in the dependent claims.

The present invention is based on the idea that if the signal quality in a neurofeedback system, in particular a neurofeedback system using dry electrodes, is limited, the user should at least be made aware of the reliability of the neurofeedback. Moreover, the system must be capable of providing feedback in real-time. Furthermore, the system should be particularly well-suited for use by non-professional users. Conventional neurofeedback systems use wet electrodes that are applied by trained professionals. This involves an adjustment of individual electrodes and impedance measurement of individual electrodes. However, electrodes, for example on the back of the skull, cannot be checked conveniently by the user himself. Furthermore, conventional neurofeedback systems are used in laboratories. The present invention is designed for real-time neurofeedback in real-life, non-laboratory situations. In real-life situations, there are two major problems.

Firstly, large signal drifts can be caused by placing or readjusting the electrodes on a user's head (using some form of a headset for the mounting) and due to the friction between the skin and the electrode due to the movements. The user might take off and put back the system on a number of times. Just taking off and putting back the electrodes would produce huge signal drifts. In addition, the circuitry used for amplifying the biofeedback signal might need certain time to stabilize. Drifts can also be introduced by movement artifacts—physical movement of the head, i.e. due to static discharge produced when rubbing dry electrodes to skin and/or hair, or due to the changes in the size and shape of the electrode-skin contact surface—produced by movement or readjustment of the electrodes' positions.

A second problem is the impact of environmental noise and noise produced by muscle tension and dynamics of such noise over time. Such noise can result in the distortion of the spectral content of the signal that can change from moment to moment. These changes can be due to changes in the environment itself, due to a user being in motion or moving from one to the other segment in the environment. The impact of electromagnetic waves (e.g. power line noise) might be completely different in different segments of the environment or might change if a person or electronic components are in the vicinity of objects made of conductive material, or if the person is in direct contact with them (e.g. metal table, chair with metal elements). The problem of signal drifts or spectral distortions can be introduced at any point in time.

Therefore, a system for neurofeedback applications needs to rely on real-time signal analysis method that can detect these problems and can be used to modify the feedback in real-time. The real-time processing introduces the requirement to use fairly simple methods to detect these problems. The proposed neurofeedback system uses signal features that can be identified using signal processing that requires very low computational power. Furthermore, the method can reuse the procedure of spectral analysis that is typically applied in many practical applications, such as EEG applications. Therefore, such signal features can be identified without demanding computations and can be implemented in software or hardware components that perform signal processing at very low cost.

In conventional neurofeedback systems, the system is set up and configured in a lengthy procedure before the actual measurement in the laboratory. At the moment when the actual neurofeedback session starts, a trained professional has ensured that the signal quality is sufficiently well and as the neurofeedback session is carried out in a controlled environment of a laboratory, the biofeedback signal quality does not change significantly during the session. Moreover, the user does not move. In this static environment with laboratory grade signal quality, the user is provided with neurofeedback. In contrast to conventional neurofeedback systems, the proposed neurofeedback system can be used in non-laboratory situations where signal drifts and spectral distortions are to be expected as described above. Hence, the feedback unit not only provides neurofeedback to the user but also provides feedback about the biofeedback signal quality. This modification prevents the user from adhering to the wrong neurofeedback in moments when the biofeedback signal quality, in particular in the frequency range of interest for the neuro feedback, is lower than required. In other words, the proposed neurofeedback system estimates the amounts of drifts in the biofeedback signal and biofeedback spectral content distortions in a computationally efficient way and uses these estimated values to modify the feedback.

It shall be noted here that the biofeedback signal is to be understood as any electrical signal that can be measured by the electrode and that represents any biological activity of the user. Such biofeedback signals include, but are not limited to, a brain activity (EEG) signal, an ECG (electrocardiography) signal, a heart rate signal, a breathing rate signal, i.e. generally any brain and/or body signal.

In one embodiment of the neurofeedback system according to the present invention, the electrode is a dry electrode. An advantage of dry electrodes is that they can be applied by the user himself. Further the application of conducting gel to the hair of the user can be avoided.

In a further embodiment of the neurofeedback system according to the present invention, the neurofeedback system is a real-time neurofeedback system adapted to provide the user with feedback in real-time. The feedback comprises both the neurofeedback as well as feedback about the biofeedback signal quality. Hence, a reduced biofeedback signal quality can be directly detected during a neurofeedback session. For example, if there is a problem with the measured biofeedback signal from an electrode, this can be indicated to the user so that the user can readjust the electrode. This is a significant improvement over conventional neurofeedback systems, wherein an entire neuro feedback session has to be repeated, for example if an electrode uses skin contact. Alternatively, the real-time information about signal quality can be used to monitor the duration of a neurofeedback session For example if a neurofeedback session of a predetermined duration is desired, only that time is counted towards the neurofeedback session, wherein the biofeedback signal is of sufficient quality. A time wherein the biofeedback signal quality is low can be discarded.

In a further embodiment of the neurofeedback system according to the present invention, the measured biofeedback signal is segmented into time segments. The signal characteristic and/or the biofeedback signal quality is determined for each time segment independently. The time segments are also referred to as epochs. Segmentation is particularly advantageous for neurofeedback systems designed for low computational power or low power consumption since the size of the biofeedback signal to be processed is limited. The length of the time segments can be equal or different for different signal characteristics or for different signal features of the measured biofeedback signal. In a variant of this embodiment, the time segments that the biofeedback signal is segmented into overlap. For example the duration of an epoch is 1 second and the next epoch of 1 second duration can start 0.25 s after the current one. In that case, the neurofeedback can be updated every 0.25 s. In a further example, a segment of a first duration is used to delineate a signal drift, whereas a segment of a second duration is evaluated to analyze a spectral content of a signal.

In a further embodiment of the neurofeedback system according to the present invention, the biofeedback signal is an EEG signal and the signal characteristic of the measured EEG signal comprises a spectral power in an EEG frequency band. This spectral power can directly represent the neurofeedback. Alternatively, the signal characteristic is a combination of a plurality of spectral powers in different EEG frequency bands or a ratio of spectral powers in EEG frequency bands. For example, the signal characteristic can be pure alpha brain wave activity or a ratio of alpha power over beta power that is presented to the user as neurofeedback. Typically, neurofeedback protocols use a relative spectral power of one of the EEG bands: alpha, beta, gamma, delta, theta (normalized to e.g. 1-40 Hz) or a ratio of band spectral powers, such as alpha/theta, beta/theta, and the like. Furthermore, different electrodes can be evaluated such as a ratio of the spectral power in a single EEG band over electrodes on the left and right brain hemisphere or the like.

In an alternative embodiment of the neurofeedback system according to the present invention, the signal characteristic of the measured biofeedback signal and/or the signal feature of the measured biofeedback signal comprises at least one element of a group of elements comprising a minimum value of the measured biofeedback signal, a maximum value of the measured biofeedback signal, a mean value of the measured biofeedback signal, a median value of the measured biofeedback signal, a standard deviation of the measured biofeedback signal, a slope of the measured biofeedback signal, a difference between the maximum and the minimum of the measured biofeedback signal, a difference between the mean and the median value of the measured biofeedback signal, a spectral power of the measured biofeedback signal in the delta frequency domain from 1 to 4 Hz, a spectral power of the measured biofeedback signal in the theta frequency domain from 4 to 8 Hz, a spectral power of the measured biofeedback signal in the alpha frequency domain from 8 to 12 Hz, a spectral power of the measured biofeedback signal in the beta frequency domain from 12 to 30 Hz, a spectral power of the measured biofeedback signal in the low gamma frequency domain from 30 to 45 Hz, a spectral power of the measured biofeedback signal in the high gamma frequency domain from 50 to 75 Hz. Alternative definitions of spectral ranges are within the scope of the present embodiment. For example, the delta frequency domain can be defined up to 4 Hz, the alpha frequency domain from 8 to 13 Hz, the beta frequency domain from 13 to 30 Hz, and one gamma frequency domain from 30 to 100 Hz. The bands can be directly adjacent, overlapping or have gaps in between. The probability of a measurement error can be calculated for each signal feature independently. Hence, the biofeedback signal quality can be determined for each signal feature independently. Alternatively, the probabilities of a measurement error for a plurality of signal features are combined to obtain a combined biofeedback signal quality. Methods for combination comprise addition, multiplication or may also include weighting factors. For example, the signal feature "slope" can have a stronger impact on signal quality than for example a "minimum value" of the measured biofeedback signal. In a variant of this embodiment, a spectral power or spectral power ratio is used for neurofeedback while signal features such as signal drift, maximum amplitude, mean, etc. are used for estimating a signal quality.

In a further embodiment of the neurofeedback system according to the present invention, a probability distribution of said probability of a measurement error is inferred from a predetermined distribution of said signal feature without measurement error. An advantage of this embodiment is the low computational effort to determine a probability of a measurement error which in turn represents the biofeedback signal quality. Alternative to determining a probability of a measurement, it is of course possible to determine a probability of an absence of a measurement error. The probability of an absence of a measurement error is one minus the probability of a measurement error. The probability distribution can be obtained from previous measurements of said signal feature in a setting where there are no measurement errors present. For example, the probability distribution is derived from a prior measurement of said signal feature in a laboratory setting under controlled conditions. Additional signal processing can be applied to the measured distribution such as low-pass filtering, smoothening or fitting to mathematical models such as a Gaussian distribution. The probability distribution can be stored in a memory of the neurofeedback system. An individual probability distribution can be stored for each signal feature. An identified signal feature is compared to the pre-defined values, e.g. maximum, minimum, expected distribution, that depict the expected range of the feature. It the signal features matches the expected distribution or is within given ranges this corresponds to a good signal quality.

In a variant of this embodiment, the predetermined distribution of the signal feature is a user-specific distribution. An appropriate distribution can be selected by the user or medical personnel. Alternatively, the predetermined distribution is based on user data such as age, gender or further information from a medical history or comparable cases. Further alternatively, the predetermined distribution is automatically determined depending on the user and/or user environment. For a manual adaptation of the predetermined distribution wherein the user selects distribution model and parameters, the neurofeedback system can further comprise a user interface. Alternatively for an automatic selection and/or adaptation, the distribution can be derived from historic data of the user. Further alternatively, segments of the biofeedback signal can be marked as a "clean signal" by the user and act as a reference for a signal without or low measurement error.

In a further embodiment of the neurofeedback system according to the present invention, the signal feature is represented by a feature value and the probability of a measurement error is obtainable from a function of probability of a measurement error over feature value. An advantage of this embodiment is the very low complexity of arriving at a probability of a measurement error from a measured signal feature. A measured signal feature is reduced to a feature value. The probability of a measurement error is a function of this feature value. The functional relationship between probability of a measurement error and feature value can comprise a prohibited range of feature values where the probability of a measurement error is 100%, an optimal range, where the probability of the measurement error is 0%, and a transition, for example a linear transition between these ranges. Alternatively, the functional relationship between measurement error and feature value is defined by a different distribution, such as a Gaussian distribution.

In a further embodiment of the neurofeedback system according to the present invention, the biofeedback signal quality is determined from a plurality of signal features of the biofeedback signal by combining the probabilities of a measurement error for each of the signal features. For obtaining more reliable information about the signal quality, a plurality of signal features of the biofeedback signal can be evaluated. For each of those signal features, a feature value can be extracted and the probability for this feature value determined. The error probabilities of the individual features can be combined in order to obtain an overall biofeedback signal quality.

In a further embodiment of the neurofeedback system according to the present invention, the neurofeedback system comprises a plurality of electrodes wherein a biofeedback signal is measured for each of the electrodes, and wherein the probability of a measurement error of a signal feature is determined for each of the biofeedback signals, wherein the biofeedback signal quality is determined by combining the probabilities of a measurement error. Advantageously, the biofeedback signal quality is not only determined from a biofeedback signal of a single electrode, but from the biofeedback signals of a plurality of electrodes. Furthermore, the biofeedback signal quality can be determined from a plurality of signal features from the biofeedback signals of a plurality of electrodes. This increases the reliability and accuracy of the determined biofeedback signal quality.

In a further embodiment of the neurofeedback system according to the present invention, a refreshment of the feedback provided to the user depends on the biofeedback signal quality. Feedback about the biofeedback signal quality can be provided to the user either explicitly or implicitly. In explicit feedback, the feedback about the biofeedback signal quality is decoupled from the neurofeedback mechanism. For example, information about a biofeedback signal drift can be rendered as a red traffic light that signals the user that he should not follow the neurofeedback if the light is red. Similarly, audio messages (e.g. beeps or announcements) can be used to signal the user that there are spectral distortions present in the signal, making him aware that he should not trust the regular neurofeedback. Furthermore, the loudness (or other aspects) of the audio signal or the intensity (or other aspect) of the traffic light can indicate the severity of spectral distortions or drifts, respectively. Alternative optical, audio or audiovisual means are within the scope of this embodiment. In implicit feedback, the biofeedback signal quality is fed back to the user by affecting the neurofeedback mechanism. For example, if the biofeedback signal quality is poor, the feedback unit does not refresh the neurofeedback. Alternatively, the feedback unit reacts only to a minor extent to changes in the signal characteristic of the measured biofeedback signal that represent the neurofeedback. When the distortion is not prominent any more (e.g. when the probability of a measurement error is back to a low value), the regular neurofeedback mechanism can resume. By providing feedback about the signal quality, implicitly or explicitly, the user is made aware that there are issues with the signal quality and that he should try to overcome them to ensure the highest effectiveness of neurofeedback. This can be done by repositioning the electrodes, avoiding head or body movements and motion, or by entering an environment where he can expect less electromagnetic interference.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Figure 1:
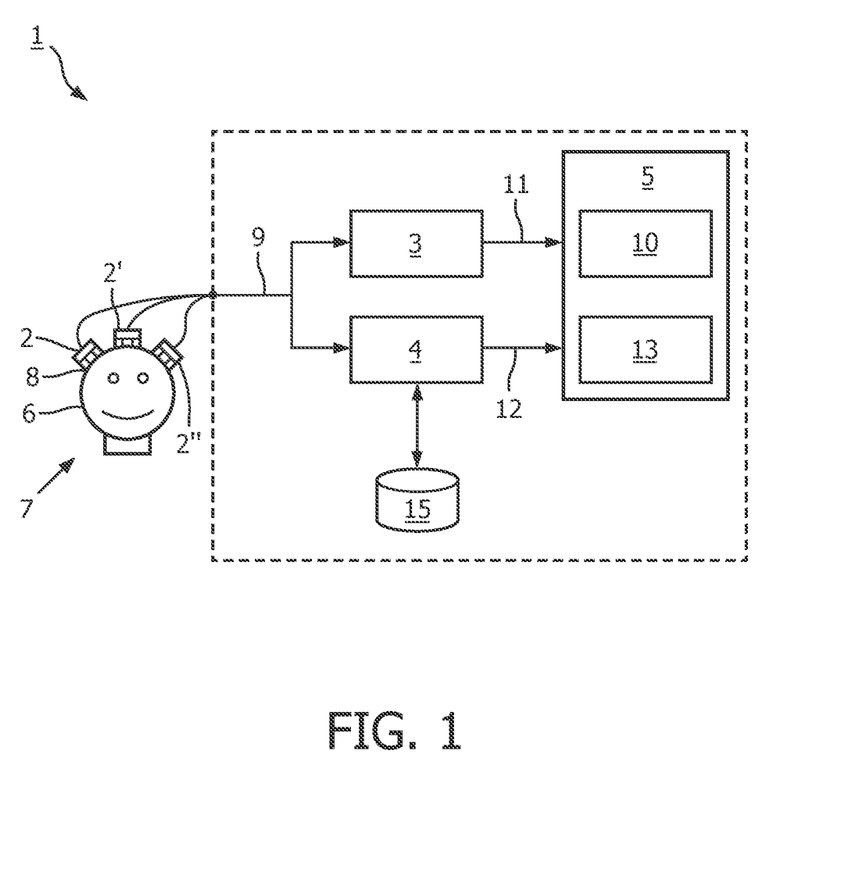
FIG. 1 shows a block diagram of a neuro feedback system according to the present invention.

FIG. 1 shows a block diagram of a neuro feedback system 1 according to the present invention. The neurofeedback system 1 comprises an electrode 2, a first signal processing unit 3, a second signal processing unit 4 and a feedback unit 5. Optionally, the neurofeedback system 1 comprises further electrodes 2', 2" and a memory 15.

The electrodes 2, 2', 2" in this embodiment are dry electrodes that contact the skin 6, in particular the scalp, of the user 7 via pin-like contact structures 8. The electrodes 2, 2', 2" are used to measure a biofeedback signal 9 of the user 7. For the following explanation an EEG signal will be used as non-limiting example.

The first signal processing unit 3 is adapted to determine a signal characteristic 11 of the measured EEG signal 9. The signal characteristic 11 in the present example is alpha brain wave activity or, in other words, the spectral power of the measured EEG signal 9 in the alpha frequency domain from 8 to 12 Hz. Alternatively, the signal characteristic 11 is a ratio of alpha power over beta power. The signal characteristic 11 can be used for neurofeedback by presenting this signal characteristic 11 as a value or as a graph over time to the user 7 on the feedback unit 5. In particular, the signal characteristic 11 can be fed back to the user 7 as a graph over time on a display 10 of the feedback unit 5.

The second signal processing unit 4 is adapted to determine an EEG signal quality 12 of the measured EEG signal 9 by extracting a signal feature of the measured EEG signal 9 and calculating a probability of a measurement error for said signal feature. This probability of a measurement error represents the EEG signal quality 12. The signal processing is described in more detail further below with reference to FIG. 2. Optionally, the memory 15 is connected to the second signal processing unit 4.

The feedback unit 5 is adapted to provide feedback to the user 7. This feedback comprises the neurofeedback represented by the signal characteristic 11 from the first signal processing unit 3 and feedback about the EEG signal quality 12 from the second signal processing unit 4. Feedback about the EEG signal quality 12 can be provided to the user 7 either explicitly or implicitly. For explicit feedback, the feedback unit 5 comprises an optional signaling means 13 adapted to provide the user 7 with feedback about the EEG signal quality 12. The signaling means 13 can be an optical signaling means, for example similar to a traffic light indicating a good EEG signal quality 12 with green light or no light and indicating a poor EEG signal quality 12 with a red light. Alternatively, this signaling means can continuously change its color from green to red, vary its intensity based on the EEG signal quality 12, change a flashing frequency, or the like. Further alternatively, the signaling means 13 can be any type of acoustical signaling means that explicitly provides the user with feedback about the EEG signal quality 12. As a second option, feedback about the EEG signal quality 12 can be implicitly provided to the user 7 by modifying the neurofeedback. For example, if the neurofeedback is provided to the user 7 as a graph over time on a display 10, the color of the curve of the graph or of the background of the graph or intensity can indicate the EEG signal quality 12. Further alternatively, as an example for implicit feedback, the refreshment of the neurofeedback presented on the display 10 may depend on the EEG signal quality 12. For example, the refreshment rate can be high at high EEG signal quality 12 and low at low EEG signal quality 12.

In a further example, in the case of alpha-based neurofeedback, the value of the relative alpha spectral power, i.e. power in the frequency range of 8 to 12 Hz compared to the power in the frequency range of 4 to 35 Hz, is translated into a "temperature bar" that indicates the signal characteristic 11. This signal characteristic 11 can be presented to the user on a display 10 of the feedback unit 5 as neurofeedback. A high value of this ratio indicates a relaxed state of the user 7. In the case of implicit feedback, an increase or decrease of the temperature bar can be diminished based on the absolute value of the EEG signal quality 12. In the case of audiovisual or purely audio signaling, the frequency of a sound or its loudness can be correlated with the EEG signal quality 12.

Figure 2:
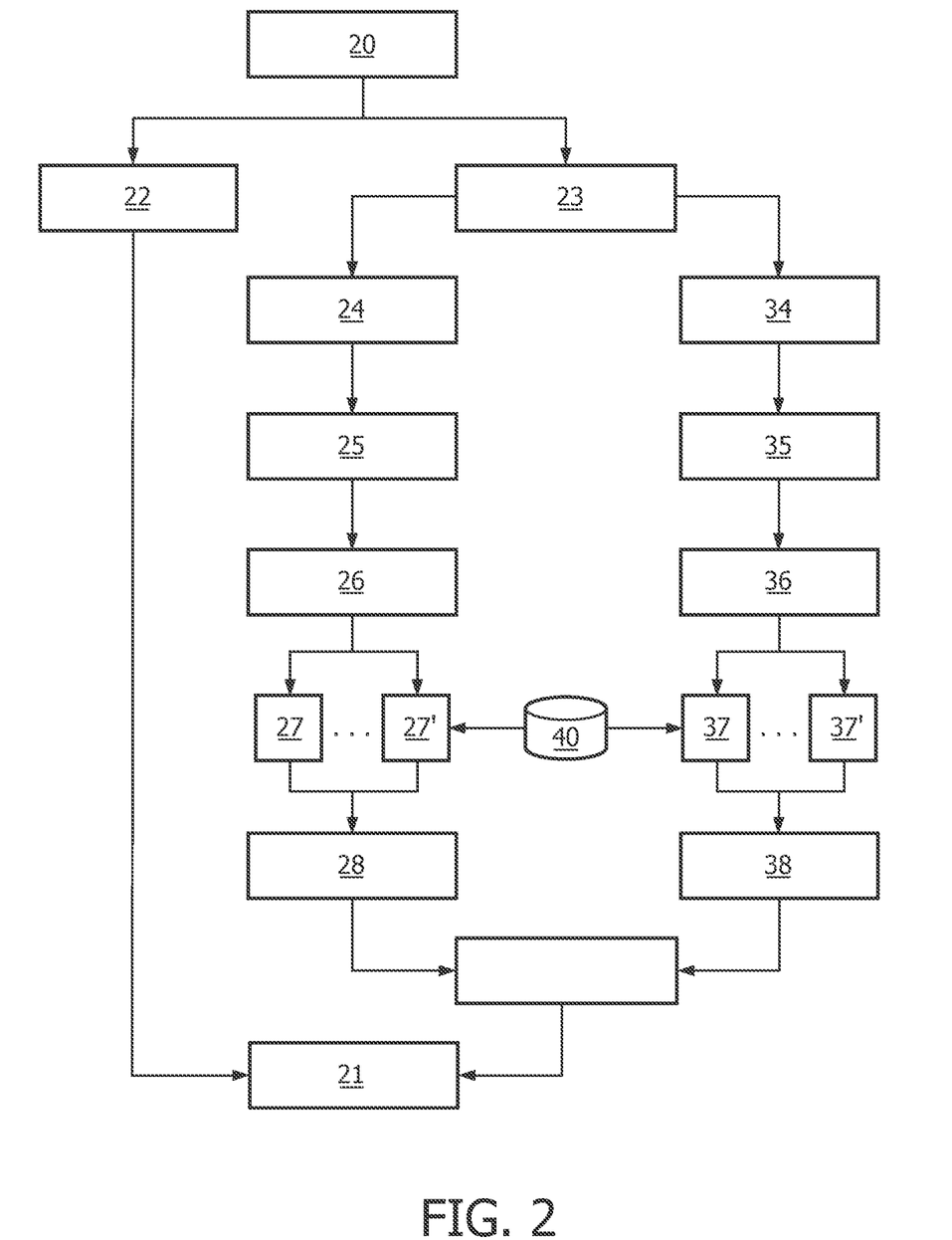
FIG. 2 shows a flow chart of the signal processing of the neurofeedback system according to the present invention.

Referring to FIG. 2, a flow chart of the steps performed by the neurofeedback system 1 is presented. The process starts with acquiring 20 a measured EEG signal 9 and ends with providing feedback 21 including neurofeedback and feedback about the EEG signal quality 12 to a user 7.

The left branch of the flow chart shown in FIG. 2 comprises the step 22 of determining a signal characteristic of the EEG signal 9. As described above, the signal characteristic presented as neuro feedback is typically a spectral power in an EEG spectral band.

The right branch of the flow chart shown in FIG. 2 provides details about the signal processing for determining an EEG signal quality. In a first step 23, the EEG signal is separated two sub-branches. In the following, features generally relating to temporal distortions or drift are dealt with in the left sub-branch and features relating to spectral distortions in the right sub-branch.

During the explanation of the process steps of FIG. 2, reference will be made to FIGS. 3 to 11 that represent graphs of the signal or signal processing results at various steps of the flow chart of FIG. 2.

Figure 3:
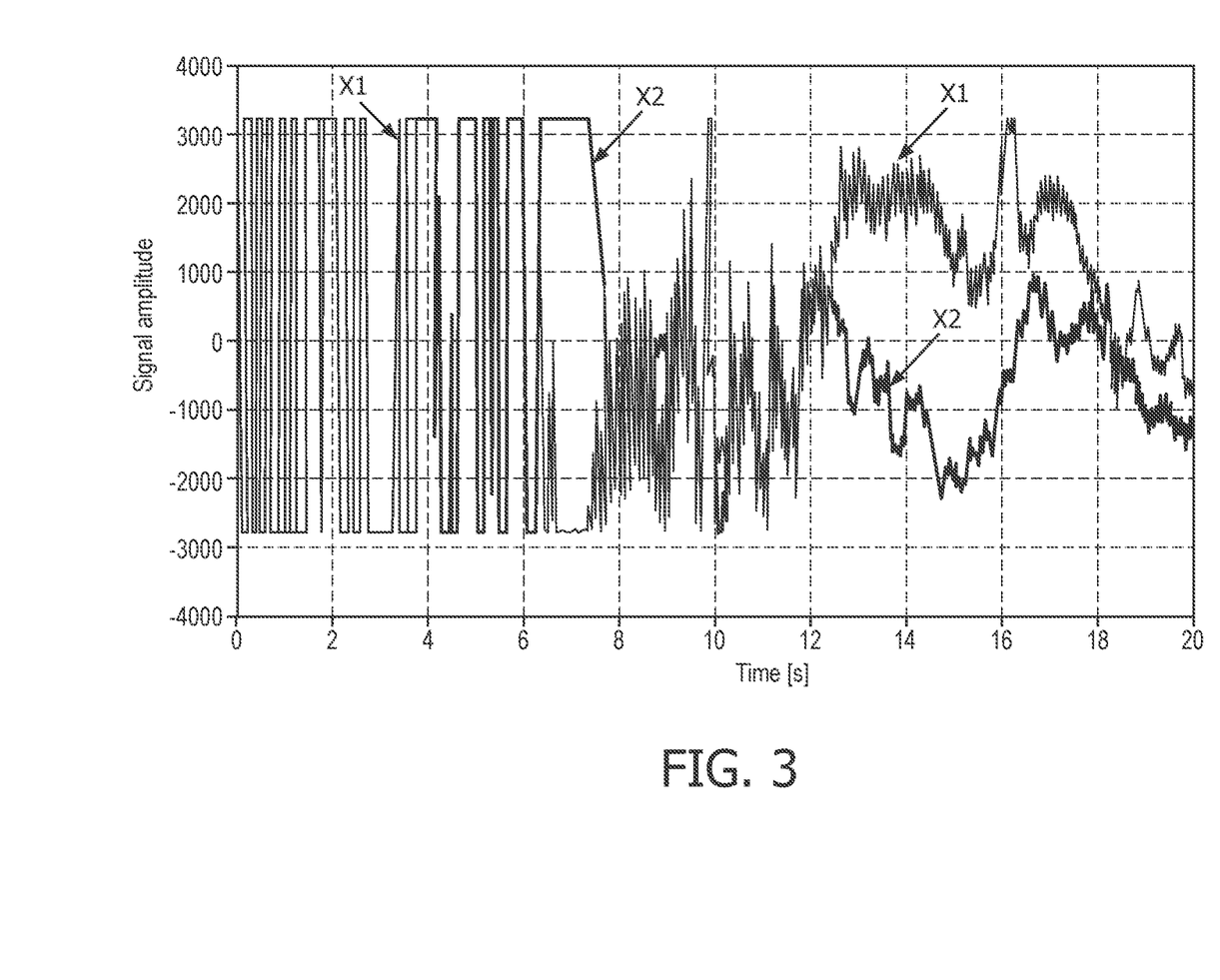
FIG. 3 shows a graph of a signal amplitude of two measured EEG signals over time for two dry electrodes.

FIG. 3 shows a graph of signal drifts produced when the user positions the dry electrodes, here in the form of an EEG headset, on his head. The dotted line represents a first signal X1 measured with a first dry electrode positioned at location C4 of the international 10-20 System for EEG measurements and referenced to the right earlobe. The dashed line represents a second signal X2 measured with a second dry electrode positioned at location C3 and referenced to the left earlobe. Due to a limited dynamic range extremely high and extremely low values are clipped. The signals vary significantly until they stabilize towards the end of the graph on the right side. In particular between 0 and 8 seconds, the signal quality is poor and should not be used for neurofeedback. Preferentially, the user only adheres to neurofeedback when the signals have stabilized.

Referring back to the left sub-branch in FIG. 2, the EEG signal is segmented 24 into temporal signals called epochs. Optionally, the epochs are overlapping. For each epoch, one or more features of the signal are extracted 25, said features including a minimum value of the signal within the epoch, a maximum value of the signal within the epoch, a mean value, a median value, a standard deviation or a slope of the signal. In an optional step 26, these features are further reduced to a difference between the maximum and the minimum value of the signal within the epoch, a difference between the mean and median value of the signal within the epoch, the standard deviation and the slope of the signal.

With respect to the right sub-branch in FIG. 2 regarding spectral distortions, the first step is a segmentation step 34 of the temporal EEG signal that is followed by a transformation 35 into frequency domain. Optionally, signal processing steps can be shared between the left and right branch of the flow chart. For example, the result of the transformation 35 into frequency domain of the right branch can be shared with step 22 in the left branch for efficient implementation. It should be noted that segmentation 24 and segmentation 34 can alternatively be one common operation common for both sub-branches. However, it is also possible to use a different segmentation for each branch or even for each signal feature within a branch. The result of the conversion into frequency domain 35 is shown in FIGS. 4a and 4b.

Figure 4A:
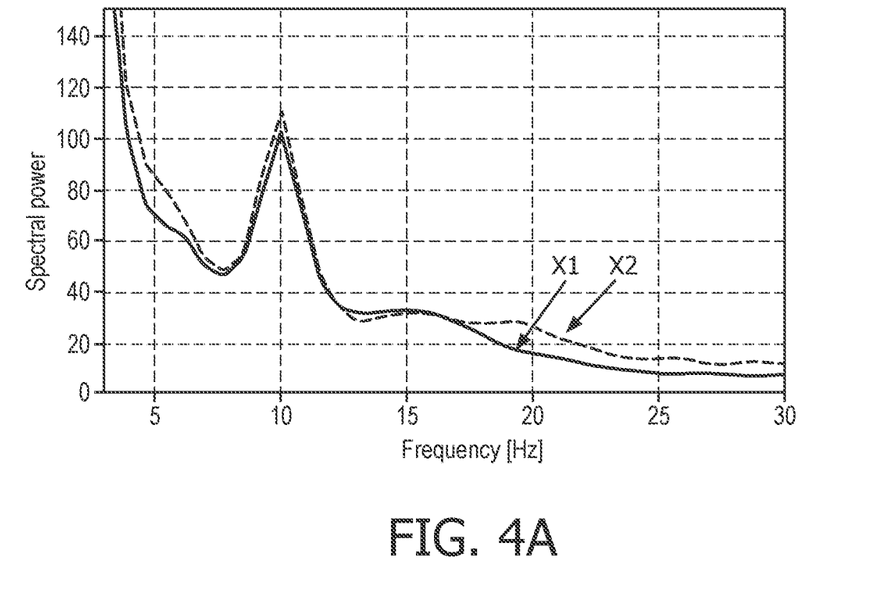
FIG. 4a shows a graph of a spectral power of two measured EEG signals without spectral distortions.
Figure 4B:
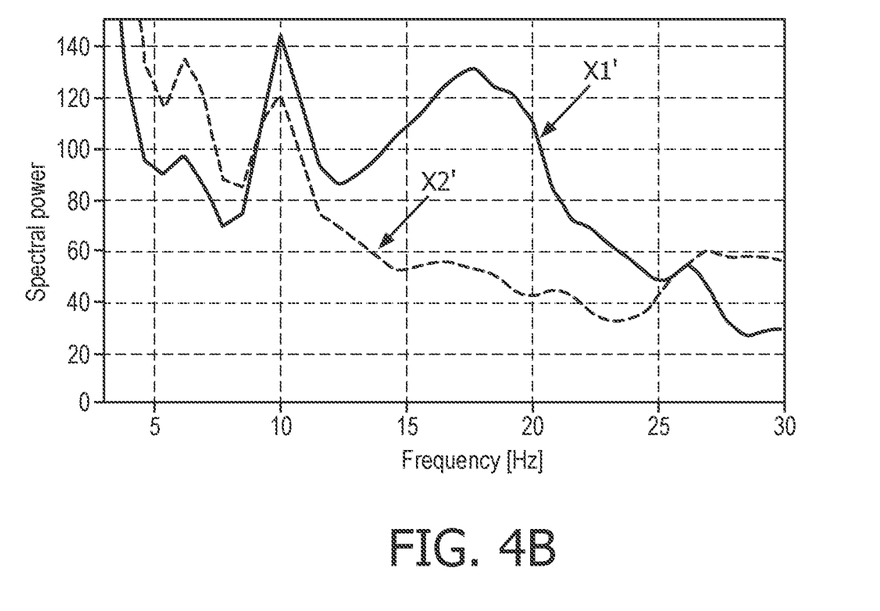
FIG. 4b shows a graph of a spectral power of two measured EEG signals with spectral distortions.

FIG. 4a shows the spectral power over frequency up to 30 Hz. Curves X1 and X2 refer to signals from two different EEG electrodes. In step 36 in FIG. 2, spectral features are extracted from the frequency domain signal, for example a spectral power in the measured EEG signal in the delta frequency domain from 1 to 4 Hz, in the theta frequency domain from 4 to 8 Hz, in the alpha frequency domain from 8 to 12 Hz, in the beta frequency domain from 12 to 30 Hz, in the low gamma frequency domain from 30 to 45 Hz, in the high gamma frequency domain from 50 to 75 Hz.

In FIG. 4a there is a strong spectral power in the alpha frequency domain that can be clearly distinguished from the spectral power in the beta frequency domain. In FIG. 4b, additional spectral distortions are present that significantly increase the spectral power in the beta frequency domain from 12 to 30 Hz, in particular for curve X1'.

There is a plurality of distortions present in EEG signals. In particular, the raw EEG signals acquired with dry electrodes are by far inferior to EEG signals measured with conventional "wet" electrodes in a laboratory setting under controlled conditions. Hence, a real-time feedback comprising neuro feedback and feedback about the EEG signal quality is desirable. However, the solution should be cheap, fast and cost-effective. According to an embodiment of the present invention, the probability of a measurement error is calculated for each feature based on the temporal and spectral feature extracted as a result of steps 25, 26 and 36, respectively. The process will be illustrated for exemplary features in the following.

Figure 5A:
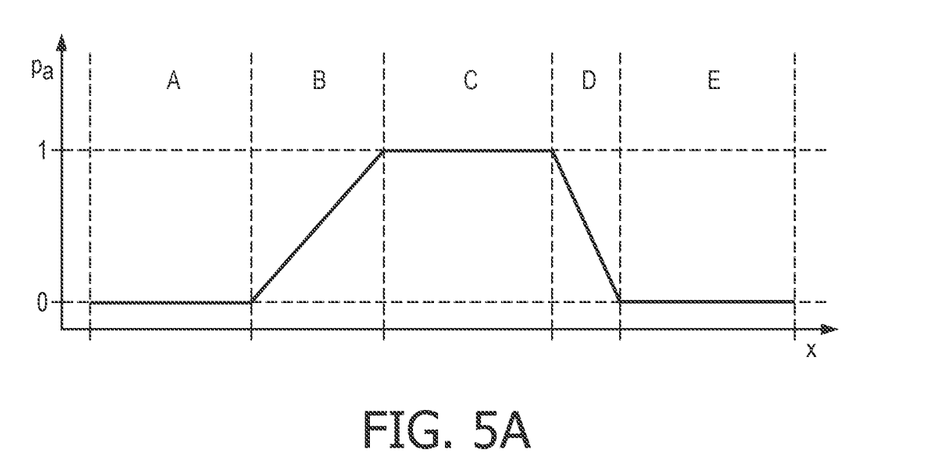
FIG. 5a shows a first graph of a function of a probability of an absence of a measurement error over feature value.
Figure 5B:
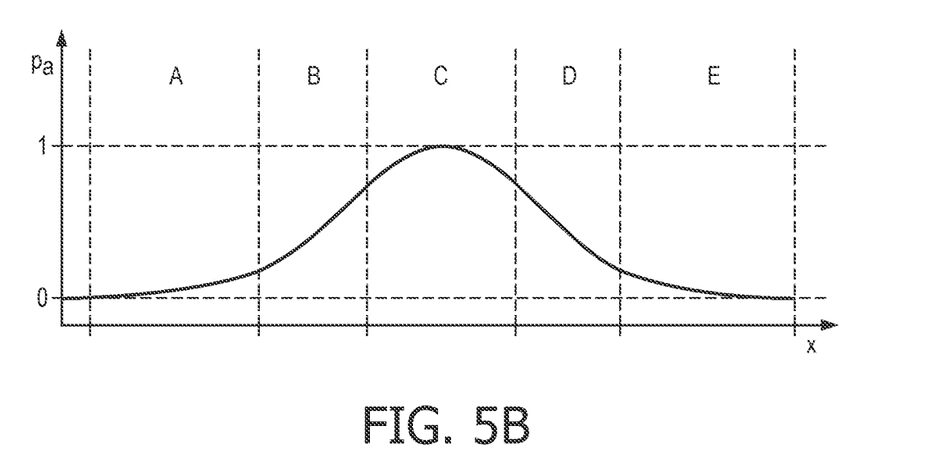
FIG. 5b shows a second graph of a function of a probability of an absence of a measurement error over feature value.

FIG. 5a shows a graph of a probability of an absence of a measurement error $p_a$ on the y-axis over the feature value x on the x-axis. Capital letters A, B, C, D and E denote different value ranges of the signal feature x. For simplicity, the graph defines a range of optimal values C, where the feature values are expected to be in, and two prohibited ranges A and E, where the feature values are not expected to be in. The range in between the two is modeled as a linear increase B or a linear decrease D from optimal to prohibited range. Alternatively, a different distribution can be applied as shown in FIG. 5b. Further alternatively, not all of the ranges must be present, for example range C with 100% probability of absence of a measurement error may stretch all the way down to a feature value of 0. In that case, ranges A and B are not present. Furthermore, the distribution can be different for each temporal and/or spectral feature. Referring to FIG. 2, the corresponding distribution can be stored in the database and received from the storage 40 for each of the features.

Figure 6A:
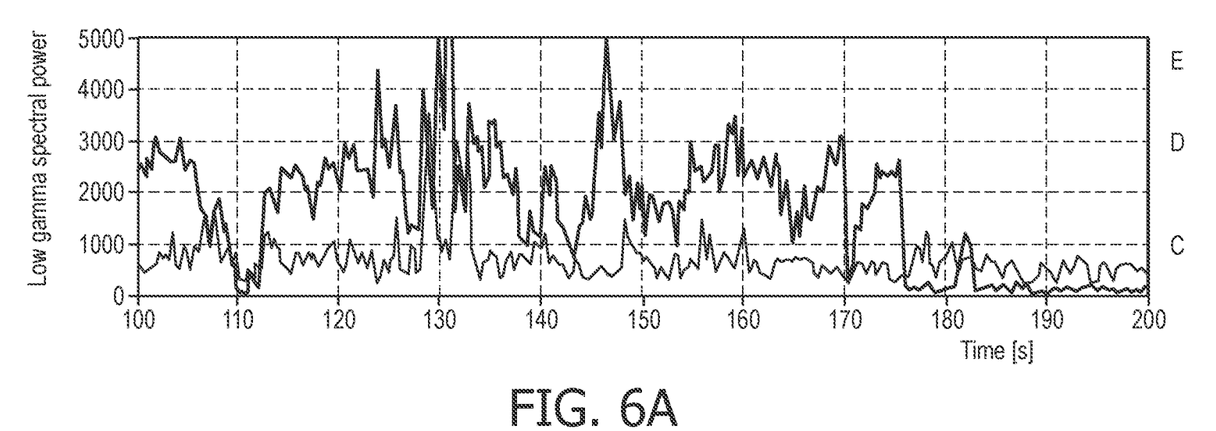
FIG. 6a shows a graph of a spectral feature of two measured EEG signals over time.
Figure 6B:
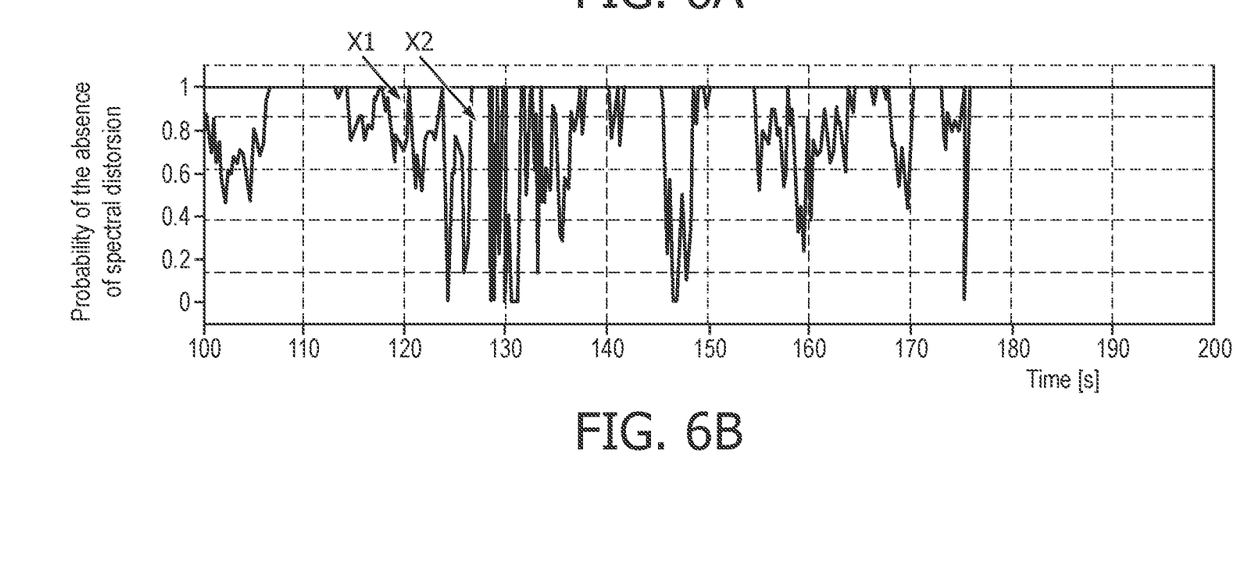
FIG. 6b shows a corresponding probability of an absence of spectral distortion over time.

FIG. 6a shows a graph of the spectral feature "low gamma spectral power" over time. Again the signals X1 and X2 of two different electrodes are depicted. The value range on the y-axis from 0 to 2000 corresponds to range C in FIG. 5a, the value range from 2000 to 4000 corresponds to value range D and the value range above 4000 corresponds to value range E. Ranges A and B are not available in this example. For each feature value in FIG. 6a, a corresponding probability of an absence of a measurement error, in this case the probability of the absence of spectral distortion, is calculated. If the low gamma spectral power of X1 or X2 is within range C, the corresponding probability of the absence of spectral distortion is 100%. This also indicates an excellent EEG signal quality. Any value in range E corresponds to a 0% probability of the absence of spectral distortion, hence, to a poor EEG signal quality. In between in range D, the corresponding probability of the absence of spectral distortion is calculated based on the function depicted in FIG. 5a, range D. This concept of calculating a probability of a measurement error for each signal feature has a low computational complexity and thereby reduces the complexity and cost of the neurofeedback system. It also is well suited for real-time implementation.

Figure 7A:
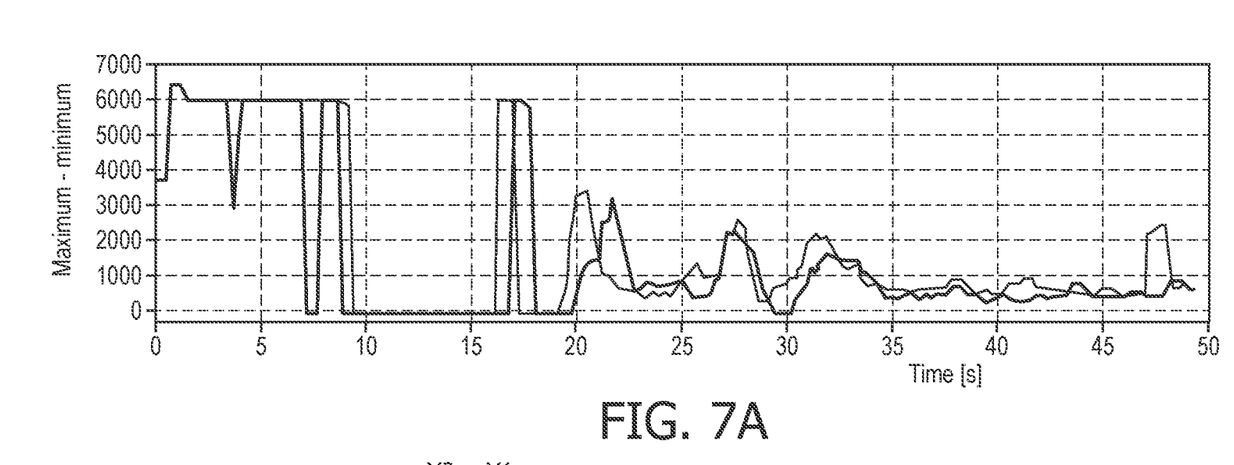
FIG. 7a shows a graph of a temporal feature value of two measured EEG signals over time.
Figure 7B:
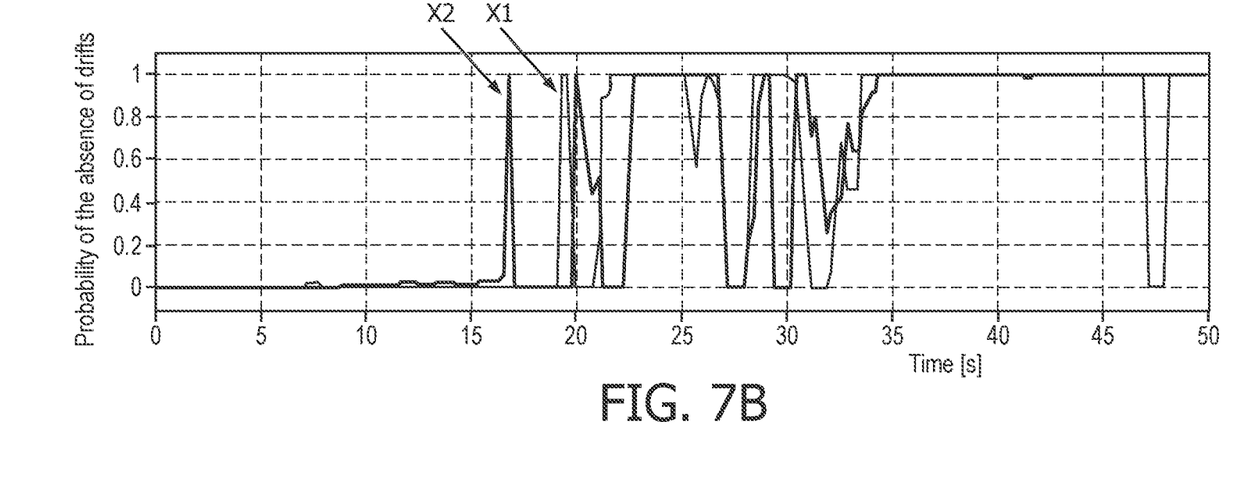
FIG. 7b shows a corresponding probability of an absence of EEG signal drift over time.

FIG. 7a shows a graph of the temporal feature, i.e. the difference of maximum and minimum signal value. Each value of the curves corresponds to the feature value extracted for a segment of the measured EEG signal. In this example, all value ranges A to E from FIG. 5a are present. A very large difference between maximum and minimum indicates a measurement error because of strong signal drift. Equally, an extremely low difference is not realistic either because a noiseless signal is also not realistic. A very low or even zero difference of maximum and minimum value occurs for example when the measured EEG signal is out of range and the signal remains at an upper or lower boundary throughout that time segment (see first few seconds of FIG. 3). In between is an optimal range C neighbored by linear transitions B and D. For each feature value in FIG. 7a, there is a corresponding probability of the absence of drifts depicted in FIG. 7b. At the beginning up to about 30 seconds, there are strong signal variations when the user adjusts the EEG electrodes on his head. During this phase, it is not reasonable to provide neurofeedback to the user because the EEG signal quality is low. Alternatively feedback about the signal quality is provided to the user in parallel to the neurofeedback to indicate a sufficient signal quality has not been reached yet.

Referring again to the flow chart in FIG. 2, the step of calculating 27, 27', 37, 37' a probability of a measurement error for one or more temporal and/or spectral signal features is indicated with $p_{t1} \ldots p_{tm}$ and $p_{f1} \ldots p_{fm}$.

Figure 8A:
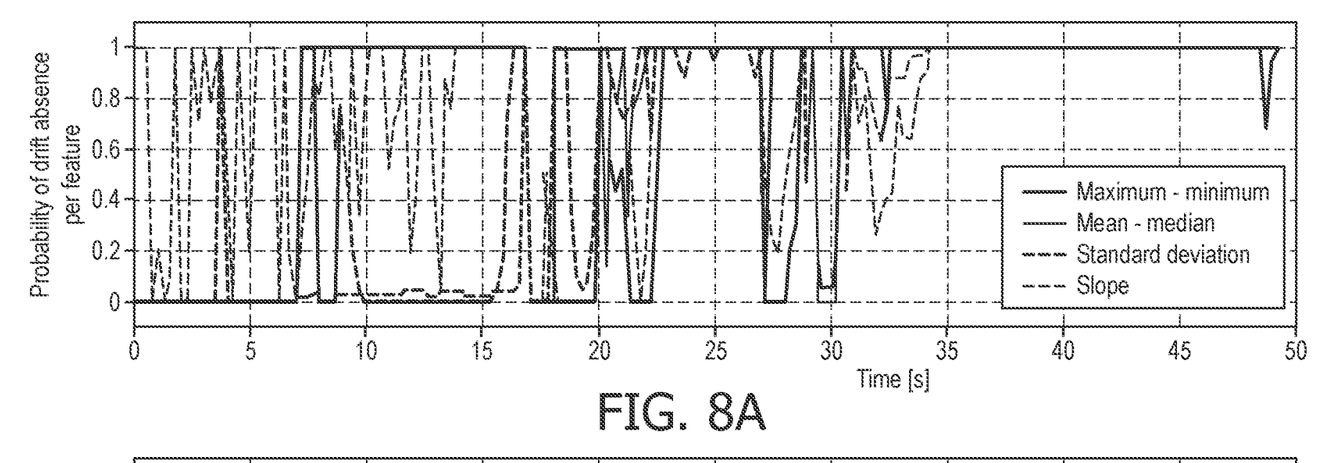
FIG. 8a shows a graph of a probability of drift absence over time for a plurality of temporal features.
Figure 8B:
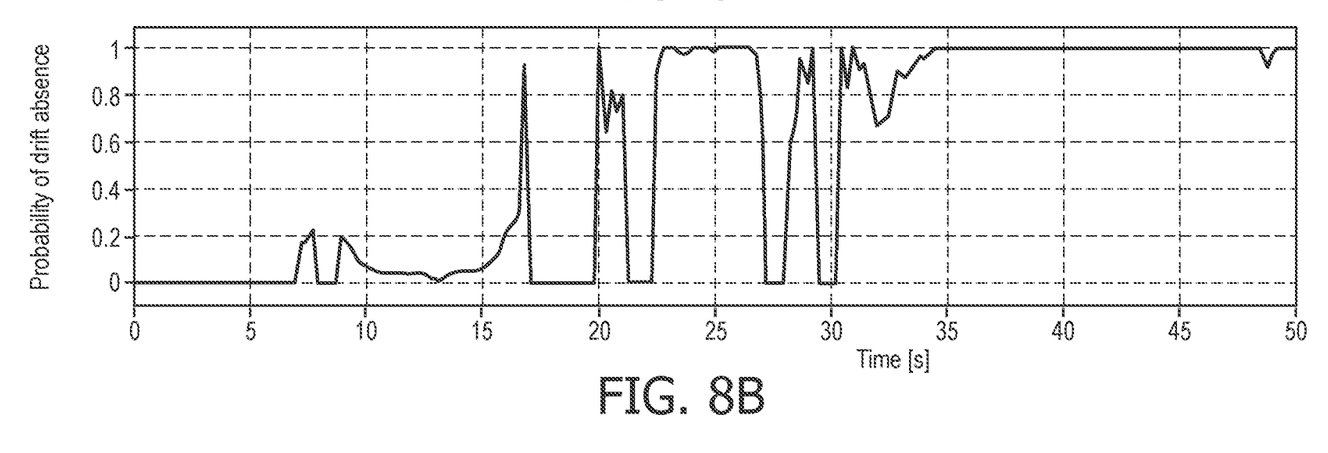
FIG. 8b shows a graph of the corresponding combined probability of drift absence over time.

FIG. 8a shows a graph of the probability of drift absence for a plurality of features. FIG. 8a depicts the temporal features maximum-minimum, mean-median, standard deviation and slope. In FIG. 8b, these features are combined in one single probability of drift absence for the temporal features. This combination can be done for example as a multiplication of the individual probabilities of the individual features.

Figure 9A:
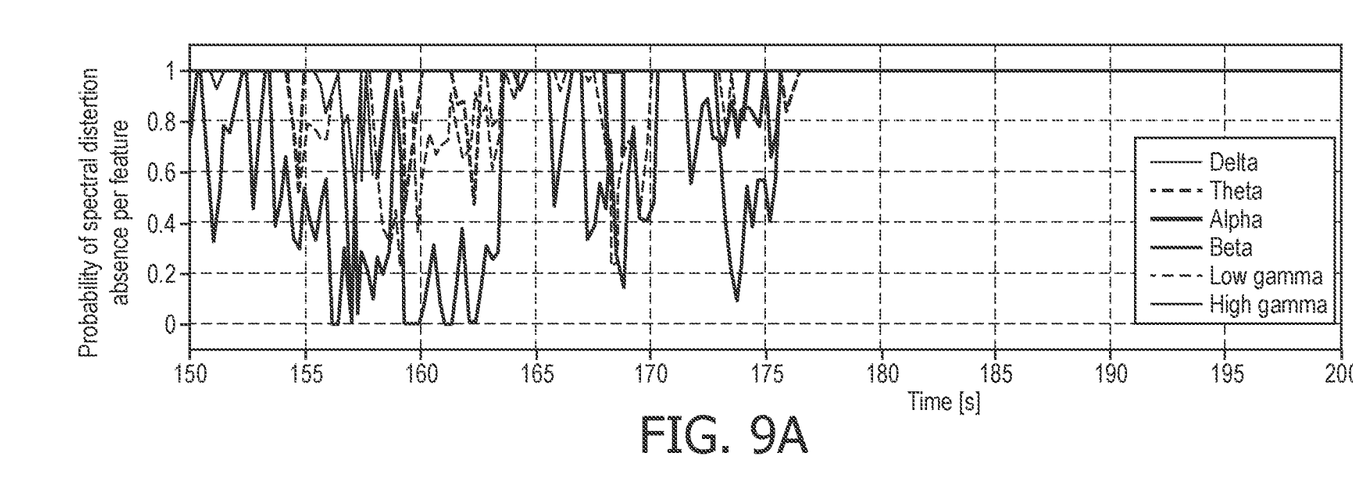
FIG. 9a shows the probability of spectral distortion absence over time for a plurality of spectral features.

Accordingly, FIG. 9a shows the probability of a spectral distortion absence per feature for a plurality of different spectral features. The combined overall probability of spectral distortion absence is presented in FIG. 9b.

Figure 9B:
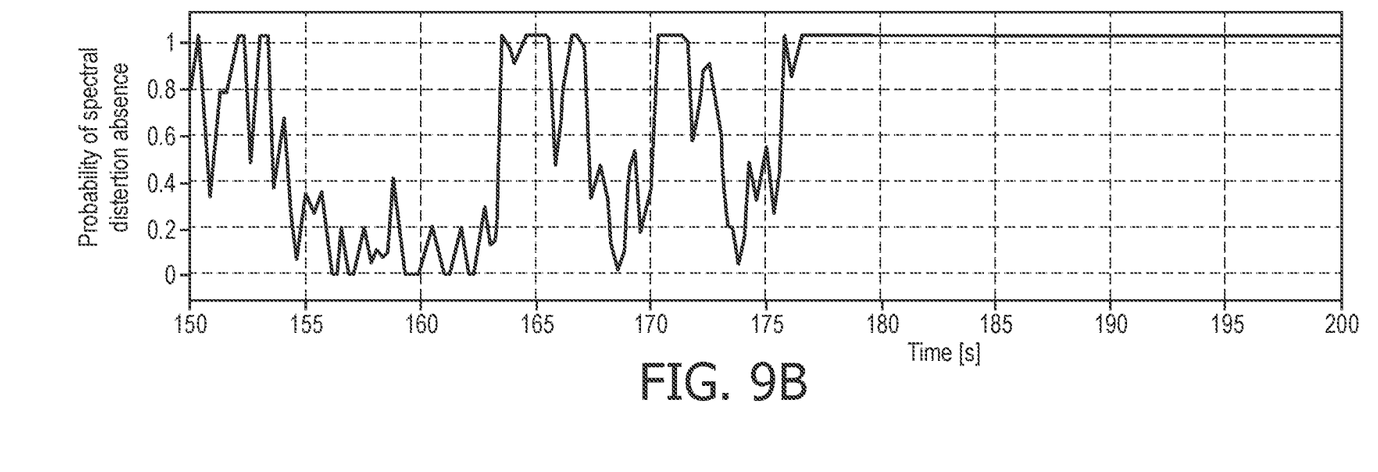
FIG. 9b shows a graph of the corresponding combined probability of spectral distortion absence over time.

Referring back to FIG. 2, the combination of FIG. 8 is carried out in step 28, wherein the combination of FIG. 9 is carried out in step 38. The combination steps are optional. The calculated probabilities of steps 28 and 38 can optionally be combined in step 50. The result is a signal quality that is supplied to the step of providing feedback 21 to the user.

Figure 10:
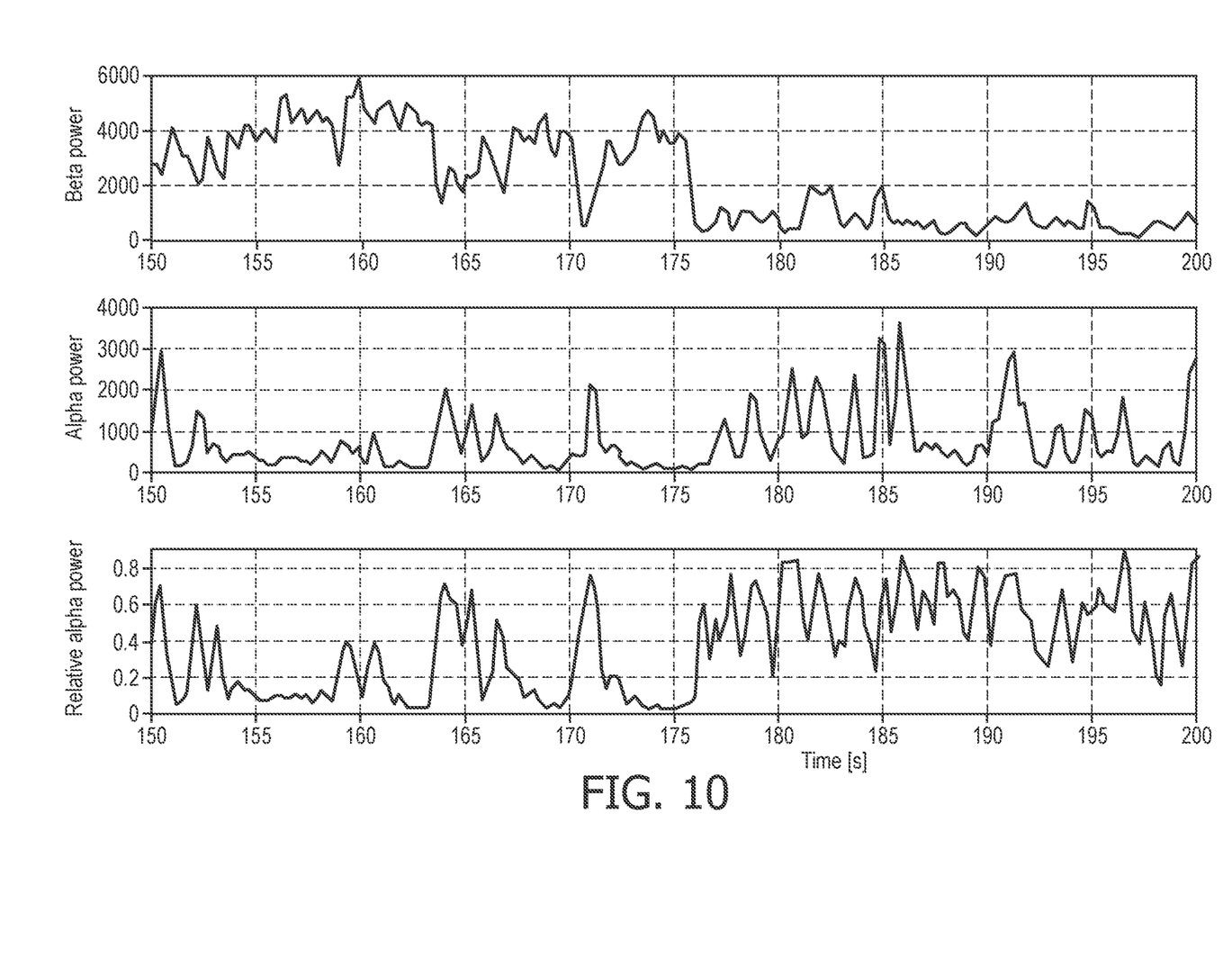
FIG. 10 shows graphs of a beta power, an alpha power and a relative alpha power over time.

An example of spectral distortions that can affect relative alpha neurofeedback is presented in FIG. 10. The figure depicts a beta power in the beta frequency band (upper graph), an alpha power in the alpha frequency band (middle graph) and the changes in the relative alpha power (lower graph). The relative alpha power is defined as the ratio of alpha power over beta power. The increase in relative alpha power after second 175 is mainly due to the absence of distortions in the beta band and less due to an increase of power in the alpha band. Feedback about this distortion prevents the user from adhering to the wrong neurofeedback.

In conclusion, the neurofeedback system, signal processor and method according to the present invention enables more robust neurofeedback, in particular using dry electrodes, and increases the effectiveness of the neurofeedback by taking into account the quality of the measured EEG signal with efficient, real-time capable signal processing.

The teachings of the present can also be applied in the field of brain-computer-interfaces (BCI). The term neurofeedback as used within the context of the present invention also comprises BCI applications. In particular, a type of neurofeedback is seen in the reaction of a computer, control unit or gaming device on EEG signals of the user.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A neurofeedback system, comprising:
a plurality of electrodes for contacting skin of a user when measuring a biofeedback signal of the user; and
at least one processor configured to:
segment the biofeedback signal into time segments;
determine, for each time segment of the time segments, a plurality of signal characteristics of each particular time segment of the measured biofeedback signal, wherein the plurality of signal characteristics represent neurofeedback,
determine, for each signal characteristic of the plurality of signal characteristics of the particular time segment, a biofeedback signal quality of the particular time segment of the measured biofeedback signal by:
extracting a signal feature corresponding to a particular signal characteristic of the particular time segment of the measured biofeedback signal, wherein extracting the signal feature corresponding to the particular signal characteristic of the particular time segment includes determining a signal drift for the particular time segment, and
calculating, based on the signal feature, a measurement error for the signal feature relative to an expected range of signal feature values accessible to the at least one processor; and
cause feedback to be provided to the user, wherein the feedback characterizes the neurofeedback based on the plurality of signal characteristics and biofeedback based on the signal quality of the time segments, and
wherein the feedback is provided by causing one or more display devices that are in communication with the at least one processor to:
display a color graph that, is based on the neurofeedback for the time segments, and
illuminate with a corresponding color of light, wherein the corresponding color of light is indicative of the biofeedback signal quality and signal drift for the time segments.

2. The neurofeedback system according to claim 1, wherein the plurality of electrodes are dry electrodes.

3. The neurofeedback system according to claim 1, wherein the at least one processor is further configured to cause the one or more display devices to illuminate with a particular intensity of light that is based an amount of signal drift for the time segments.

4. The neurofeedback system according to claim 1, wherein the measured biofeedback signal is a measured EEG signal and each signal characteristic of the plurality of signal characteristics of the measured EEG signal corresponds to a particular frequency band.

5. The neurofeedback system according to claim 4, further comprising: calculating a probability of measurement error for the signal feature by comparing the signal feature to an expected range of values.

6. The neurofeedback system according to claim 4, wherein the plurality of signal characteristics include at least two adjacent EEG frequency bands.

7. The neurofeedback system according to claim 1, wherein a refreshment of the feedback provided to the user depends on the biofeedback signal quality.

8. A method implemented by one or more processors, the method comprising;
segmenting a measured biofeedback signal into time segments, the measured biofeedback signal provided by a plurality of electrodes contacting skin of a user,
determining, for each time segment of the time segments, a plurality of signal characteristics of the time segment of the measured biofeedback signal, wherein the plurality of signal characteristics represent neurofeedback;
determining, for each signal characteristic of the plurality of signal characteristics of each particular time segment of the time segments, a biofeedback signal quality, wherein the biofeedback signal quality of the particular time segment of the measured biofeedback signal is determined by:
extracting a signal feature corresponding to a particular signal characteristic of the particular time segment of the measured biofeedback signal, wherein extracting the signal feature corresponding to the particular signal characteristic of the particular time segment includes determining signal drift for the particular time segment, and
calculating a measurement error for the signal feature relative to an expected range of signal feature value, and
causing feedback to be provided to the user via an audio interface or visual interface, wherein the feedback characterizes the neurofeedback based on the plurality of signal characteristics and biofeedback based on the signal drift for the time segments.

9. The method according to claim 8, wherein the plurality of electrodes are dry electrodes.

10. The method according to claim 8, wherein the feedback is provided to the user in real-time.

11. The method according to claim 8, wherein the measured biofeedback signal is a measured EEG signal and each signal characteristic of the plurality of signal characteristics of the measured EEG signal corresponds to a particular frequency band.

12. The method according to claim 8, further comprising: calculating a probability of measurement error for the signal feature by comparing the signal feature to an expected range of values.

13. The method according to claim 8, wherein the plurality of signal characteristics include at least two adjacent EEG frequency bands.

14. The method according to claim 8, wherein a refreshment of the feedback provided to the user depends on the biofeedback signal quality.

15. A non-transitory computer-readable medium configured to instructions that, when executed by one or more processors, cause the one or more processors to perform operations that include:
  segmenting a measured biofeedback signal into time segments, the measured biofeedback signal provided by a plurality of electrodes contacting skin of a user,
  determining, for each time segment of the time segments, a plurality of signal characteristics of the time segment of the measured biofeedback signal, wherein the plurality of signal characteristics represent neurofeedback;
  determining, for each signal characteristic of the plurality of signal characteristics of each particular time segment of the time segments, a biofeedback signal quality, wherein the biofeedback signal quality of the particular time segment of the measured biofeedback signal is determined by:
    extracting a signal feature corresponding to a particular signal characteristic of the particular time segment of the measured biofeedback signal, wherein extracting the signal feature corresponding to the particular signal characteristic of the particular time segment includes determining signal drift for the particular time segment, and
    calculating a measurement error for the signal feature relative to an expected range of signal feature value, and
  causing feedback to be provided to the user via an audio interface or visual interface, wherein the feedback characterizes the neurofeedback based on the plurality of signal characteristics and biofeedback based on the signal drift for the time segments.

16. The non-transitory computer-readable medium according to claim 15, wherein the plurality of electrodes are dry electrodes.

17. The non-transitory computer-readable medium according to claim 15, wherein the measured biofeedback signal is a measured EEG signal and each signal characteristic of the plurality of signal characteristics of the measured EEG signal corresponds to a particular frequency band.

18. The non-transitory computer-readable medium according to claim 17, wherein the operations further include: calculating a probability of measurement error for the signal feature by comparing the signal feature to an expected range of values.

19. The non-transitory computer-readable medium according to claim 17, wherein the plurality of signal characteristics include at least two adjacent EEG frequency bands.

20. The non-transitory computer-readable medium according to claim 15, wherein a rate of refreshment of the feedback provided to the user is directly proportional the biofeedback signal quality.

* * * * *